United States Patent [19]

Uzgiris

[11] 4,011,044
[45] Mar. 8, 1977

[54] USE OF LASER SPECKLE PATTERNS FOR MEASUREMENT OF ELECTROPHORETIC MOBILITIES

[75] Inventor: Egidijus E. Uzgiris, Schenectady, N.Y.

[73] Assignee: General Electric Company, Schenectady, N.Y.

[22] Filed: July 6, 1976

[21] Appl. No.: 702,941

[52] U.S. Cl. .......................... 23/230 B; 23/253 R; 204/180 R; 204/299 R; 424/12
[51] Int. Cl.² .................. G01N 27/26; G01N 33/16
[58] Field of Search .................... 23/230 B; 424/12; 204/180 R, 299 R

[56] References Cited

UNITED STATES PATENTS

| | | | |
|---|---|---|---|
| 3,498,905 | 3/1970 | Strickler | 204/299 R |
| 3,708,402 | 1/1973 | Bean | 204/299 R |
| 3,764,512 | 10/1973 | Greenwood | 204/299 R |
| 3,766,048 | 10/1973 | Flygare | 204/180 R |
| 3,783,117 | 1/1974 | Bean | 204/180 R |
| 3,793,180 | 2/1974 | Flower | 204/299 R |
| 3,819,505 | 6/1974 | Parent | 204/299 R |
| 3,855,094 | 12/1974 | Teppo | 204/299 R |

OTHER PUBLICATIONS

R. J. Cohen et al., Immunochemistry, 12(4), 349–351 (1975).

*Primary Examiner*—Joseph Scovronek
*Assistant Examiner*—Sidney Marantz
*Attorney, Agent, or Firm*—Marvin Snyder; Joseph T. Cohen; Jerome C. Squillaro

[57] ABSTRACT

Reduction in electrophoretic mobility of antigen-coated microscopic polystyrene spheres due to an antigen-antibody reaction is detected by observing changes in oscillation amplitude of speckle patterns (i.e., regions of light and dark) produced by laser light scattered by the particles as they are driven back and forth by a square wave electric field.

6 Claims, 5 Drawing Figures

USE OF LASER SPECKLE PATTERNS FOR MEASUREMENT OF ELECTROPHORETIC MOBILITIES

INTRODUCTION

This invention relates to electrophoretic mobility measurement, and more particularly to use of coherent light for visually detecting an antigen-antibody reaction.

In I. Giaever, application Ser. No. 384,113, filed July 30, 1973, abandoned in favor of continuation-in-part application Ser. No. 608,255, filed Aug. 27, 1975 and assigned to the instant assignee, it is pointed out that immunological reactions are highly specific biochemical reactions in which a first protein, denominated an antigen, combines with a second protein specific to the antigen, denominated an antibody, to form an immunologically-complexed protein. It is also pointed out therein that any arbitrary protein will adsorb onto a substrate in a monomolecular layer only, and that a specific antibody (or antigen) for such arbitrary protein will bond to the protein to form a bimolecular protein layer on the substrate.

In E. E. Uzgiris application Ser. No. 631,727, filed Nov. 13, 1975, now U.S. Pat. No. 3,984,533 and assigned to the instant assignee, presence of a specific protein in solution is detected by depositing a first protein, or antigen, on microscopic particles which, when thus coated, exhibit a certain electrophoretic mobility. If a protein which specifically reacts to the first protein, i.e., an antibody, is then combined with the first protein in a dilute solution of such antibodies, the electrophoretic mobility of the particles drops to a much lower value, since antibody molecules are of much lower mobility than most other proteins at normal pH of the solution. An electrophoretic mobility measurement of the particles then provides an indication of whether or not the specific protein sought is present in the solution.

The aforementioned Uzgiris application Ser. No. 631,727 employs photodetecting means to sense occurrence of an antigen-antibody reaction. The present invention, however, does away with need for photodetecting means or sophisticated detection instrumentation by providing a simplified qualitative method of detecting this reaction.

Speckle patterns, or regions of light and dark, arise when a laser beam is made to scatter from a solution of particles, due to interference of the scattered coherent light. Such speckle patterns are quite pronounced and are easily visible to the eye, even when the concentration of scatterers is not large. For example, measurements may be readily made with 0.81 micrometers diameter polystyrene particles (such as spheres) a a concentration of approximately $10^7$ particles/cc.

With suitable electrodes, optical cell, and square wave voltage generator, all of which are described in C. P. Bean et al. application Ser. No. 668,606, filed Mar. 19, 1976 and assigned to the instant assignee, the speckle pattern can be made to oscillate back and forth along the direction of the applied electric field as the particles are driven back and forth by the square wave electric field. This pattern of oscillation is visually observable by placing a viewing screen, which may simply comprise a white card, a suitable distance away from the scattering cell in the forward scattering direction. Amplitude of the observed oscillation depends on this distance as well as on the focusing details of the incident laser beam. However, the amplitude of oscillation is also proportional to mobility of scatterers, so that a measure of the oscillation amplitude constitutes a measure of electrophoretic mobility.

Accordingly, one object of the invention is to provide a qualitative method of detecting a change in electrophoretic mobilities of particles.

Another object is to provide a method of quantitatively measuring electrophoretic motion of particles without need for sophisticated optical detection instruments.

Another object is to provide a simplified, low-cost method of detecting an antigen-antibody reaction.

Briefly, in accordance with a preferred embodiment of the invention, a method of testing for a change in electrophoretic mobility of particles suspended in a solution comprises directing coherent light onto the solution such that light scattered from the solution impinges on a display screen in a speckle pattern configuration. A square wave voltage is applied across the solution, and movement of the speckle pattern along the direction of the applied electric field across the solution is observed. By matching a reference motion display of known parameters to movement of the speckle pattern, a measure of particle mobility may be obtained.

BRIEF DESCRIPTION OF THE DRAWINGS

The features of the invention believed to be novel are set forth with particularity in the appended claims. The invention itself, however, both as to organization and method of operations, together with further objects and advantages thereof, may best be understood by reference to the following description taken in conjunction with the accompanying drawings in which:

DESCRIPTION OF TYPICAL EMBODIMENTS

Preconditions for high sensitivity of the detection method of the invention include selection of appropriate microscopic particles, the particle concentration in a solution, and mixing procedures. Particles comprising polystyrene spheres of 0.81 micrometers diameter, dialyzed to remove surfactants and other contaminants, have been coated with antigens and suspended in solution in order to detect, by electrophoretic mobility measurements, presence of antibodies in the solution that are specific to the antigens, as stated in the aforementioned Uzgiris application Ser. No. 631,727. Particles of other material to which proteins will adsorb, such as silica, are also suitable for use in the invention. Cells, protein molecules, and in fact most colloidal particles can, in principle, be suitable since there is no requirement on shape or uniformity of size, provided the specific gravity of the particles is chosen so that they remain in suspension for at least a few minutes to allow sufficient time for optical scattering measurements to be made. For adequate sensitivity, particle concentration in solutions to be tested must not be large since total particle surface area must be kept small (much less than one square centimeter, for example, in a typical cuvette). Concentrations of $10^7$ particles per cubic centimeter, where the particles are of 0.81 micrometers diameter, have proven satisfactory in making visual measurements according to the instant invention.

Mixing has been accomplished with use of conventional magnetic turbulent stirring in a beaker and by employing electrophoretic stirring in an optical cell. Electrophoretic stirring is especially useful since it results in motion of the microscopic particles relative to the immediate surrounding liquid. For optical mixing, turbulent and electrophoretic motions may be combined.

The technique for detecting an antigen-antibody combination on a microscopic surface is dependent upon changes in electrophoretic mobility of protein-coated particles. A certain electrophoretic mobility is associated with a surface formed by an antigen deposited on a particle. If an antibody molecule then combines with that protein, mobility of the particle drops to a considerably lower value, since antibody molecules are of much lower mobility than most other proteins at normal pH. Additionally, the pH can be adjusted within a range of about pH 4.0 to pH 8.0, so that a substantial mobility difference is maintained between the antigen and antigen-antibody films. Mobility of antigen-coated particles changes by as much as a factor of two or three when antibody molecules combine with the antigen.

Figure 1:
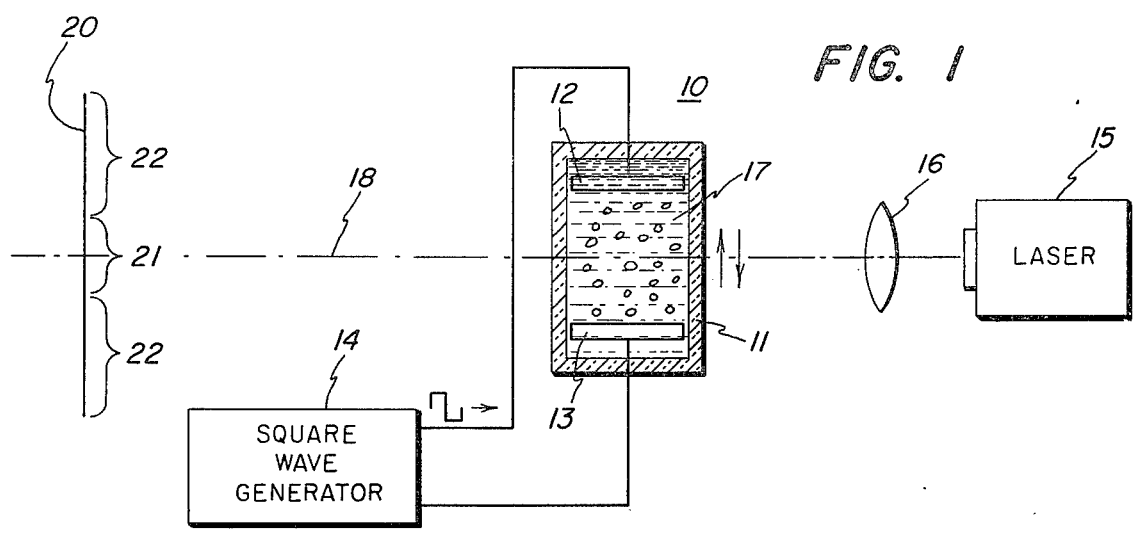
FIG. 1 is a top view schematic illustration of apparatus employed in practicing the invention.

A system for optically detecting electrophoretic mobility changes is illustrated in FIG. 1. The system comprises a cuvette or electrophoretic cell 10 including fluid containment means 11 fabricated of a light-transmissive, fluid-impenetrable material, such as glass, plastic or the like. A pair of spaced electrodes 12 and 13, included in cell 10, are preferably of rectangular shape and have mutually-parallel facing surfaces defining an interelectrode gap preferably not exceeding one millimeter in width, as described in the aforementioned Uzgiris application Ser. No. 631,727.

Container 10 is filled with a dilute colloidal suspension, typically of 0.005 Normal sodium chloride solution 17 containing the microscopic particles, and an electric field is established between electrodes 12 and 13 by square wave generator 14. The square wave generator provides electrodes 12 and 13 with constant magnitude, alternating polarity voltage.

The gap between electrodes 12 and 13 is illuminated by coherent optical energy which passes through focusing optics 16 from a laser 15. A portion of this energy passes undeviated through cell 10 along the path designated 18 and strikes a viewing screen 20, conveniently of the reflective type, in a center region 21. Most of the remaining energy is scattered by the microscopic particles within the gap between electrodes 12 and 13 so as to illuminate portions of a fringe region 22 surrounding center region 21 on screen 20. While center region 21 continuously remains brightly lit, fringe region 22 exhibits annular patterns of light and dark regions due to constructive and destructive optical interference occurring in the light emerging from cuvette 10.

Figure 2:
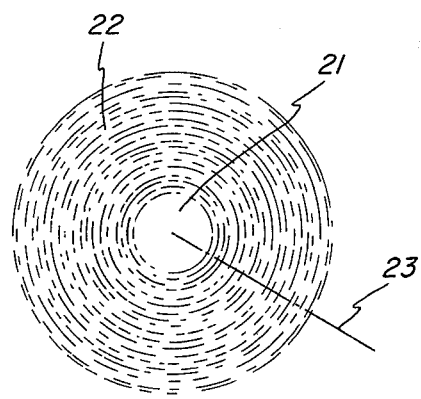
FIG. 2 is a diagramatic illustration of speckle patterns produced on the viewing screen shown in the apparatus of FIG. 1.
Figure 3:
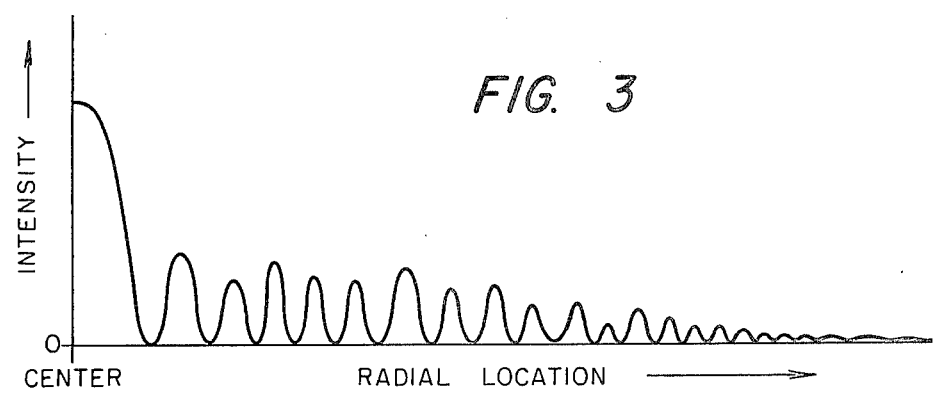
FIG. 3 is a graphical illustration of light intensity in FIG. 2 along a radial direction.

FIG. 2 is a schematic illustration of a speckle pattern produced on screen 20 in the apparatus of FIG. 1. The speckle pattern is generally comprised of a center region 21, which is brightly illuminated by the generally-unscattered portion of the laser beam, surrounded by a fringe region 22 which comprises light and dark areas in generally concentric annuli. If optical intensity is measured along any radius 23 in the speckle pattern, as shown in FIG. 2, a graphical illustration of optical intensity versus radial location in the speckle pattern may be plotted, as shown in FIG. 3. The illustration of FIG. 3 shows that while the speckle pattern is not perfectly regular, it exhibits general characteristics which do not deviate greatly from a regular pattern, hence giving rise to the possibility of deriving from the pattern information concerning the contents of cuvette 10.

Figure 4A:
FIGS. 4A and 4B are photographic reproductions of typical speckle patterns produced on the viewing screen shown in the apparatus of FIG. 1.
Figure 4B:

FIGS. 4A and 4B are photographic reproductions of actual speckle patterns formed using the apparatus illustrated in FIG. 1. (The dark bar visible in each of FIGS. 4A and 4B is a shadow cast by a stop inserted in the laser beam emerging from the cuvette in order to reduce light intensity of the center region of the speckle pattern relative to light intensity of the fringe region thereof.) The generally concentric annuli of light and dark regions are clearly visible in FIGS. 4A and 4B.

When the apparatus of FIG. 1 is operated, changes in mobility of the polystyrene spheres suspended in solution 17 due to antibodies combining specifically with antigen coatings on the spheres, are readily detected. Square wave generator 14 may produce constant voltage magnitudes of rectangular waveform ranging up to 15 volts, at any selected frequency ranging from 1 to as much as 10 Hertz. With these square wave electric field parameters, annuli in fringe region 22 of the speckle pattern shown in FIG. 2 appear to oscillate back and forth along the direction of the applied electric field as the particles in cuvette 10 are driven back and forth by the electric field in the directions indicated by the arrows in FIG. 1. While amplitude of the observed oscillation (i.e. displacement of interference fringe annuli on screen 20) depends on distance between screen 20 and cuvette 10, as well as on the focusing of the incident laser beam (i.e., the smaller the spot size of the focused beam, the larger the speckle patterns), it is also proportional to average mobility of the scattering particles suspended in solution 17 and hence the amplitude of oscillation is also a measure of the electrophoretic particle mobilities. As an example, particle motion of approximately 5 micrometers in solution 17 can cause fringe motion having a displacement measuring approximately 5 millimeters at an angle of approximately 10° from axis 18, when viewing screen 20 is approximately 50 centimeters from cuvette 10.

When antibodies in solution 17 combine specifically with the antigen-coated polystyrene spheres in suspension therein, mobility of the spheres decreases substantially, providing a clear indication or signature of the reaction. By simply placing a ruler against viewing screen 20, or by delineating distances by means of graduations or markings formed directly on the viewing screen, so as to be able to measure amplitude of observed fringe movement (i.e. by measuring linear displacement of interference fringe annuli over a predetermined period of time), a somewhat quantitative determination of average mobility value may be made, without need for photodetectors, signal amplifiers, high voltage power supplies, or frequency analyzers. The high sensitivity with which antigen or antibody levels can be probed by use of suspended particles and electrophoretic techniques is described in Uzgiris application Ser. No. 631,727. Where a high degree of precision in measurements is not required, mobility data may be obtained in accordance with the present invention at very low cost.

Quantitative measurements may be made with greater accuracy and precision by adjusting the square wave generator to drive electrodes 12 and 13 in cuvette 10 with an electric field that results in the fringe motion matching a predetermined amplitude of motion at a particular angle. For visual reference, an oscillating mirror with a light pointer (i.e., a galvanometer arrangement) can be made to superimpose an oscillating light pointer on fringe region 22 on screen 20 in the apparatus of FIG. 1. The parameters of the square wave electric field required to match the fringe region motion with the reference motion thus provide a measure of mobility of the particles under study.

The foregoing describes a method of quantitatively measuring electrophoretic motion without need for optical detection instruments. The invention also provides a qualitative method of detecting a change in electrophoretic mobilities of particles, and specifically provides a simplified, low-cost method of detecting an antigen-antibody reaction.

While only certain preferred features of the invention have been shown by way of illustration, many modifications and changes will occur to those skilled in the art. It is, therefore, to be understood that the appended claims are intended to cover all such modifications and changes as fall within the true spirit of the invention.

I claim:

1. A method of testing for a change in electrophoretic mobility of particles suspended in a solution, comprising:
    directing coherent light onto said solution such that light scattered from said solution impinges on a display screen in a speckle pattern configuration;
    applying a square wave voltage across said solution; and
    observing movement of said speckle pattern on said screen along the direction of the applied electric field across said solution.

2. The method of claim 1 wherein the step of observing movement of said speckle pattern on said screen comprises measuring linear displacement of interference fringe annuli on said screen to obtain an indication of average mobility of said particles suspended in said solution.

3. The method of claim 1 including the additional step of adjusting said square wave voltage such that said movement of said speckle pattern on said screen achieves a predetermined amplitude and frequency, said adjustment thereby being indicative of average mobility of said particles suspended in said solution.

4. A method of detecting a reaction between a first protein and a second protein comprising the steps of:
    coating said first protein on each of a plurality of microscopic particles;
    forming a dilute suspension of said particles in a solution to be tested for presence of said second protein;
    directing coherent light onto said solution such that light scattered from said solution impinges on a display screen in a speckle pattern configuration;
    applying a square wave voltage across said solution; and
    observing movement of said speckle pattern on said screen along the direction of the applied electric field across said solution.

5. The method of claim 4 wherein the step of observing movement of said speckle pattern of said screen comprises measuring linear displacement of interference fringe annuli on said screen to obtain an indication of average mobility of said particles suspended in said solution.

6. The method of claim 4 including the additional step of adjusting said square wave voltage such that said movement of said speckle pattern on said screen achieves a predetermined amplitude and frequency, said adjustment thereby being indicative of average mobility of said particles suspended in said solution.

* * * * *